United States Patent [19]
Gatti

[11] Patent Number: 5,192,276
[45] Date of Patent: Mar. 9, 1993

[54] SMOKE ASPIRATING DEVICE

[76] Inventor: John E. Gatti, 104 Treaty Elms La., Haddonfield, N.J. 08033

[21] Appl. No.: 627,769

[22] Filed: Dec. 14, 1990

[51] Int. Cl.$^5$ .............................................. A61M 1/00
[52] U.S. Cl. .................................. 604/313; 604/180; 604/317; 128/847; 15/415.1
[58] Field of Search ................... 604/19, 35, 73, 180, 604/308, 312, 313, 315, 317, 355, 356; 128/847, 863, 888, 897, DIG. 26; 15/415.1, 416, 422.1; 454/188, 191, 263, 339, 345, 370; 54/419

[56] References Cited

U.S. PATENT DOCUMENTS

| | | | |
|---|---|---|---|
| 1,053,665 | 2/1913 | Spencer | 15/415.1 |
| 3,610,238 | 10/1971 | Rich | 128/847 |
| 3,692,024 | 9/1972 | Von Otto | 128/847 |
| 3,763,857 | 10/1973 | Schrading | 128/847 |
| 3,881,477 | 5/1975 | Von Otto | 128/847 |
| 4,184,226 | 1/1980 | Loevewich | 15/415.1 |
| 4,205,668 | 6/1980 | Criddle | 128/847 |
| 4,275,719 | 6/1981 | Mayer | 128/847 |
| 4,533,352 | 8/1985 | Van Beek et al. | 604/413 |
| 4,660,388 | 4/1987 | Greene, Jr. | 454/370 |
| 4,921,492 | 5/1990 | Schultz et al. | 604/315 |
| 4,925,452 | 5/1990 | Melinyshyn et al. | 604/284 |
| 5,014,389 | 5/1991 | Ogilvie et al. | 15/415.1 |
| 5,015,243 | 5/1991 | Schifano | 604/317 |
| 5,034,006 | 7/1991 | Hosoda et al. | 604/317 |

Primary Examiner—Stephen C. Pellegrino
Assistant Examiner—Ralph A. Lewis
Attorney, Agent, or Firm—Norman E. Lehrer; Franklyn Schoenberg

[57] ABSTRACT

A smoke aspirating device is provided for eliminating smoke generated during electrocautery surgery which is simple to use and includes a substantially flat and flexible panel structure having spaced upper and lower panel members with a closed area therebetween, the upper panel member having a plurality of spaced apertures arrayed over substantially the planar area thereof connecting with the closed area, the lower panel member have a pressure sensitive adhesive coated over its lower surface for attachment to a patient and the panel structure having a connector projecting from one end which is adapted for connecting with a vacuum source for drawing smoke and air from an electrocautery surgery site over the surface of the panel structure and inwardly through the apertures and closed area within the panel structure.

8 Claims, 2 Drawing Sheets

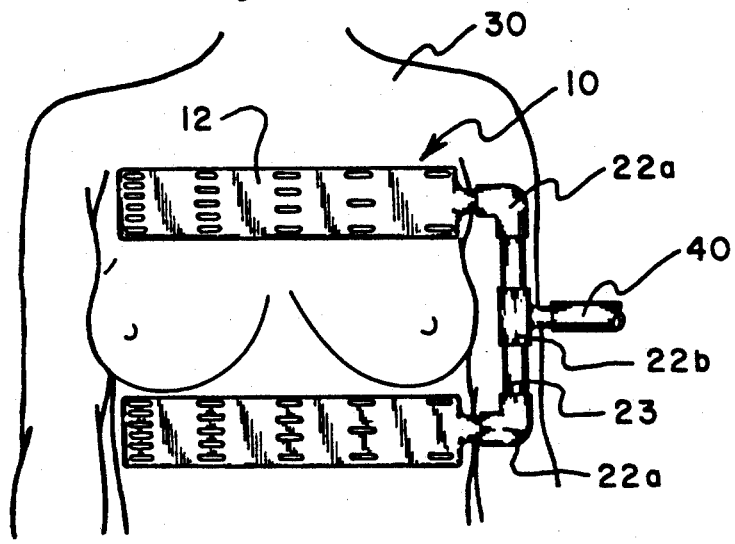
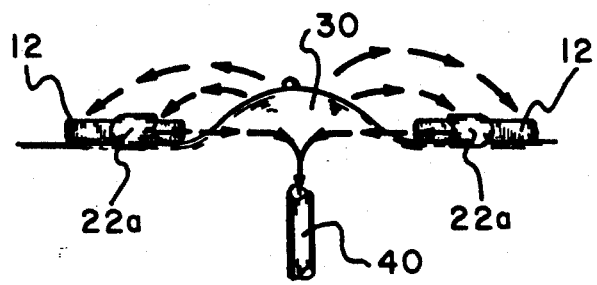
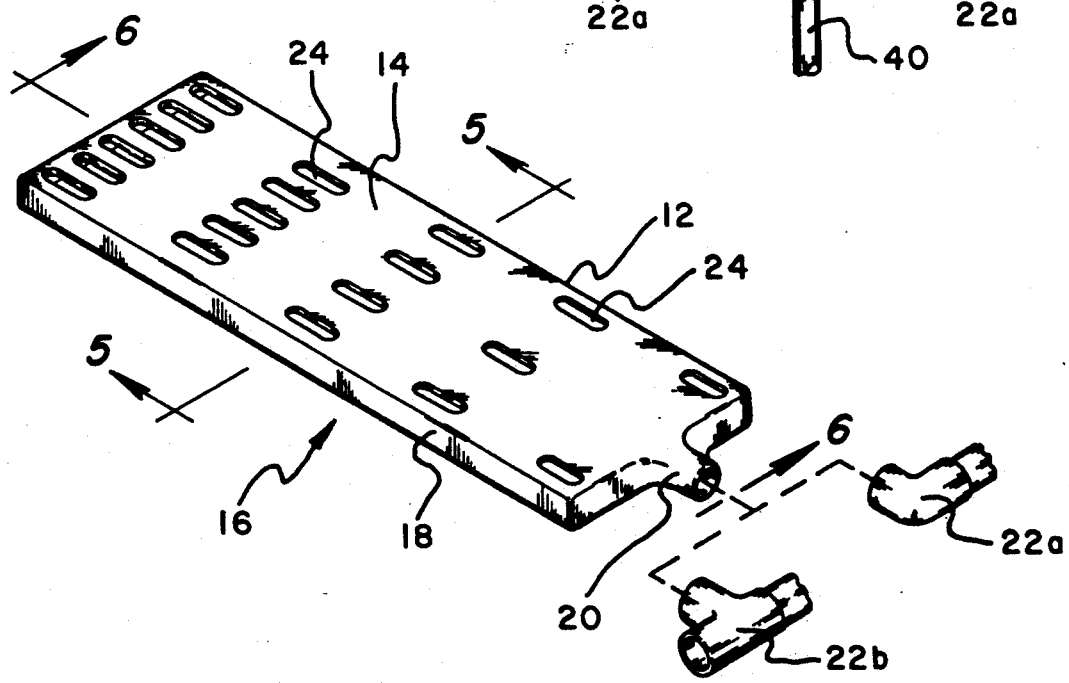

SMOKE ASPIRATING DEVICE

FIELD OF THE INVENTION

The present invention is directed to a device for eliminating smoke generated during electrocautery surgery and, more particularly, to such a device which is simple to use, which does not interfere with the operative surgeon's field of view and which is inexpensive and, therefore, disposable.

BACKGROUND OF THE INVENTION

As is well known in the art, a significant amount of blood and other body fluids, smoke and vapor are often present at an electrocautery site and are generated as a result of the electrocautery surgery. Since their presence can often render it difficult for a surgeon to see the operating site clearly, devices have been proposed in the past for removing the fluids and smoke.

U.S. Pat. Nos. 2,888,928; 4,307,720 and 4,683,884 for example, show electrosurgical instruments having a suction tube associated therewith and located in close proximity to the cauterizing blade. While such devices may have some usefulness, they are relatively expensive. Because of this, they are intended to be reused and must, therefore, be cleaned and sterilized after each use. Furthermore, these devices are not necessarily intended to be turned on at all times but are only turned on when it is desired to remove heavy accumulations of fluid and smoke. Thus, when the vacuum sources for these devices are not being operated, smoke rises from the surgery site and can be inhaled by the operating surgeon and other in the operating room.

It has been found that the smoke generated during electrocautery surgery may be carcinogenic and/or otherwise to those who may inhale the same. In U.S. Pat. No. 4,865,049 to J. E. Gatti, the present Applicant, there is disclosed a simple and inexpensive shield primarily intended to remove smoke generated during electrocautery surgery to prevent a surgeon from inhaling the same. The shield includes a flexible base member connected to a vacuum source with adjustable support means for a flexible clear sheet-like material mounted over the base member to serve as an shield enclosure about a surgery site within which any gases generated as the result of electrocautery surgery would be vented before rising above the shield to be inhaled by the surgeon. While the shield has been useful for the purpose intended, the shield interferes with access to the surgical site on some portions of a patients anatomy and to Applicant's knowledge, no one has ever proposed a simple and inexpensive device primarily intended to remove smoke generated during electrocautery surgery on any portion of a patients anatomy, let alone such a device which does not interfere with the operative surgeon's field of view or access to an electrocautery surgery site on various portions of a patient's anatomy.

Gas venting devices have been proposed for removing anesthetic gases or other fumes or dust from an operating room or a dental consultation room. Such devices are shown for example, in U.S. Pat. Nos. 3,877,691; 4,082,092 and 4,446,861. Each of these devices shows a substantially rigid gas venting shield which is mounted at the end of a support arm so that the same can be positioned where needed. Again, however, these devices are relatively expensive and must be cleaned and sterilized after each use.

Other air cleaning or gas venting devices for use in operating rooms and other hospital applications have been proposed such as disclosed, for example, in U.S. Pat. Nos. 4,063,495; 4,223,669 and 4,468,825. These devices, however, are designed for use with other medical apparatus and, thus, are also relatively expensive and intended to be reused, requiring that they be cleaned and sterilized after each use.

Masks have also been employed by surgeons and other operating room personnel to not only protect the patient but also protect the operating personnel from airborne bacteria, viruses and the like. While simple cloth-filter type masks provide some benefit, they cannot prevent significant amounts of smoke and other dangerous gases from passing therethrough. Masks which include vacuum sources therein for protecting the doctor have been proposed in U.S. Pat. No. 3,747,599. Such a mask might have some practicality when there is only one doctor present during surgery but would become impractical if each person in the operating room were wearing one. Furthermore, as with the devices discussed above, the mask shown in this patent is relatively expensive and, again, must be cleaned and sterilized after each use.

As is known, gas venting and air cleaning apparatus have been proposed for use in a variety of work situations such as disclosed, for example, in U.S. Pat. Nos. 3,719,136; 4,071,338; 4,179,984; 4,248,162; 4,596,060; 4,647,295 and 4,868,369. Such apparatus, however, is generally integral with or closely associated with worktables and the like primarily intended for particular mechanical work situations such as welding, and the gas venting apparatus is intended to be reused and is relatively expensive.

SUMMARY OF THE INVENTION

It is, accordingly, an object of the present invention to provide a smoke aspirating device which is simple to use in an operating room for eliminating smoke created during electrocautery surgery so as to prevent injury to the operating physician, the patient and other operating room personnel by inhalation of the smoke, and which is made from inexpensive materials intended to be disposable and does not interfere with the operating surgeon's field of view or access to the surgical site on any portion of the patient's anatomy.

In accordance with the present invention there is provided a smoke aspirating device for eliminating smoke generated during electrocautery surgery comprising:

an elongated substantially flat and flexible panel structure having spaced elongated upper and lower panel sections with lateral side walls extending between the corresponding marginal edges of said upper and lower panel sections and defining a closed area between said elongated panel sections, said lower panel section having releasable securing means for said panel structure and said upper panel section having a plurality of spaced apertures therethrough;

connecting means projecting from an end of said panel structure and in communication with the closed area therein;

means for connecting said connecting means to vacuum drawing source means wherein a flow of air is created from above said upper panel section inwardly through the apertures in said upper panel section and the closed area within said panel structure.

BRIEF DESCRIPTION OF THE DRAWING

For the purpose of illustrating the invention, there is shown in the accompanying drawing one form which is presently preferred; it being understood that the invention is not intended to be limited to the precise arrangements and instrumentalities shown.

FIG. 1 is a top plan view of the smoke aspirating device in accordance with the principles of the invention showing the same in use;

FIG. 2 is a schematic representation of the smoke aspirating device showing the venting of smoke from a surgery site during use;

FIG. 3 is an enlarged top perspective view of the smoke aspirating device of the invention;

DETAILED DESCRIPTION OF THE PREFERRED EMBODIMENT

Figure 4:
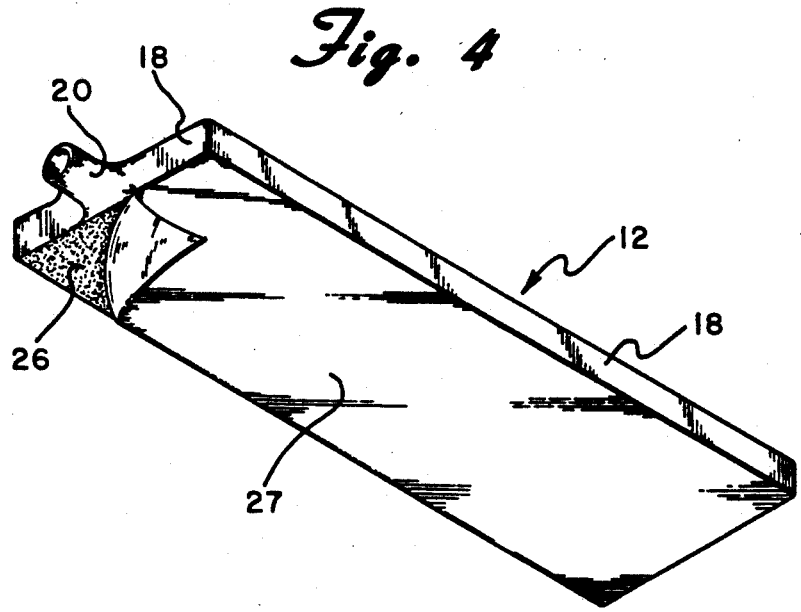
FIG. 4 is an enlarged bottom perspective view of the smoke aspirating device of FIG. 3.

Referring now to the drawing wherein like reference numerals have been used throughout the various figures to designate like parts, there is shown in FIG. 1 a smoke aspirating device in accordance with the principles of the invention designated generally as 10. The smoke aspirating device 10 including two panel structure members 12 is shown secured to opposite sides of the upper chest portion, the electrocautery surgery site, of a patient 30 lying on an operating table (not shown). The panel structures 12 of the smoke aspirating device 10 are shown as being attached directly to the patient, but they may be secured to a cloth draped over the patient. A suction hose 40 connects the smoke aspirating device 10 to a vacuum source (not shown). With the aspirating device 10 positioned in the manner shown, it is useful for removing smoke generated during electrocautery surgery on the patient's breast area as depicted by the arrows shown in FIG. 2.

Figure 5:
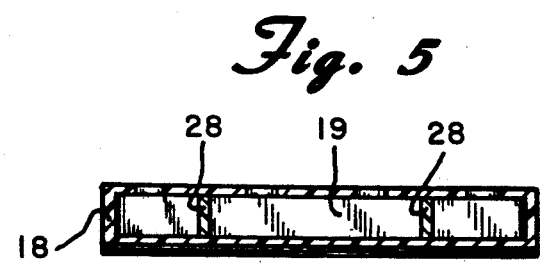
FIG. 5 is an enlarged cross-sectional view taken along the line 5—5 of FIG. 3.
Figure 6:
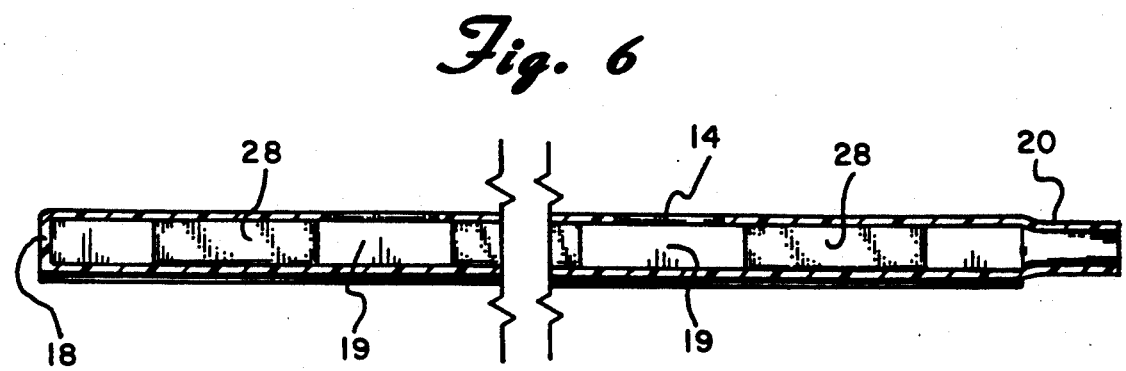
FIG. 6 is an enlarged cross-sectional view, part broken away, taken along line 6—6 of FIG. 3.

Referring now more specifically to FIGS. 3 through 6, the smoke aspirating device 10 comprises an elongated (essentially rectangular in shape) substantially flat and flexible panel structure 12 including vertically spaced elongated, substantially flat and flexible panel sections members 14 and 16. Lateral side walls 18 extend between the corresponding marginal edges of panel section members 14 and 16 and define a closed area or cavity 19 therebetween. The panel structure 12 includes a hollow cylindrically shaped outlet neck 20 at one end communicating with the closed area 19 defined, between the panel section members 14 and 16 and the lateral side walls 18. Coupler fittings 22a, 22b and tube 23 are adapted to be connected to the outlet neck 20 and to the vacuum hose 40.

The upper panel section member 14 is provided with a plurality of elongated apertures 24 which are spaced over substantially the entire plan area of the panel section member 14 and open into the closed area or cavity 19. The apertures 24 are arrayed in the upper panel section member 14 to provide for substantially uniform distribution of the flow of air and smoke over the length of the panel structure 12. As would be evident, the size, shape and array pattern of the apertures 14 through the upper panel section member 14 may be varied in accordance with the invention depending on the particular application for which the smoke aspirating device 10 is to be used. The lower panel section 16 carries a conventional pressure-sensitive adhesive coating or tape 26 over at least a portion of the bottom surface thereof, which is covered and thereby protected by a release paper 27. The release paper 27 is removed when it is desired to utilize the aspirating device 10.

To insure that the enclosed area or cavity 19 is within the panel structure 12 is maintained substantially unobstructed during operation of the smoke aspirating device 10, spaced support members 28 are located within the enclosed area 19 which may be secured to and project inwardly from lower panel section member 16 or upper panel section member 14. Alternatively, the upper and lower panel section members 14 and 16 may be provided with spaced support ribs in a conventional manner which do not substantially interfere with the flexibility of the panel structure 12.

The smoke aspirating device 10 of the invention may be fabricated by conventional techniques from a variety of flexible materials such as plastic, rubber, metal and the like. Advantageously, at least a portion of the device may be formed by conventional means as a unitary structure from thin, flexible plastic or rubber sheets or the like.

The smoke aspirating device 10 of the present invention is utilized in the following manner. The device 10 may be prepared in several sizes and configurations for use on different portions of the anatomy of a patient about to undergo electrocautery surgery. The device 10 may be used for surgery areas on the face, neck, chest, abdomen, buttocks, legs, hands, scalp and the like. Whether an aspirating device 10 with one or two panel structures 12 is employed is determined by the location and size of the surgery area involved. When, as shown in FIG. 1, the surgery site is the patients upper chest area, two panel structures 12 are concurrently used, located on opposite sides of the surgery site. After the surgery site is designated by the surgeon, the release paper 27 is removed from the pressure-sensitive adhesive 26 covering the bottom surface of the lower panel section member 16 of each panel structure 12. A panel structure 12 is secured to the patient's body on opposite sides of the surgery site with the longitudinal edge of the structure 12 adjacent and substantially parallel to that of the surgery site and with the outlet neck 20 of each structure 12 suitably aligned. The appropriate coupler fittings 22a, 22b, and/or tube 23 are then secured over the outlet neck 20 at the end of each panel structure 12 and suction hose 40 is connected to the appropriate coupler fitting.

When the vacuum source is energized, air is pulled downwardly by the array of openings 24 in each of the upper panel section members 14 so that a draft is created, as illustrated by the arrows shown in FIG. 2, along both sides of the surgery site. It can be seen, therefore, that any smoke or other gases rising from the electrocautery surgery site will be drawn from the surgery site and exhausted through the enclosed area 19 in the panel structure 12 and vacuum pump. Little, if any, of the smoke will rise from the surgery site to be inhaled by the surgeon or other personnel in the area. This will be true even with a relatively weak vacuum source once the airflow pattern in created.

From the foregoing it will be apparent that the smoke aspirating device of the invention constitutes a departure from the prior art concepts of air cleaning and gas venting devices for use in operating rooms and other hospital applications, providing a noxious gas venting system which is simple to use, does not interfere with an operating surgeons field of view or access to a surgery site during performing surgery on numerous sections of a patients anatomy and which is inexpensive and, therefore, disposable.

Having thus described the invention in relation to the drawings hereof, it will be clear that modifications could be made in the preferred embodiments without departing from the spirit of the invention. Accordingly, it is not intended that the words used to describe the invention be limiting thereof nor should the drawings be considered so. It is intended that the invention be limited only by the appended claims.

What is claimed is:

1. A smoke aspirating device for eliminating smoke generated during electrocautery surgery comprising:
    an elongated substantially flat and flexible panel structure having spaced elongated upper and lower panel members with a closed area defined therebetween, said lower panel member having releasable securing means for said panel structure adapted for mounting said panel structure on the anatomy of a patient undergoing electrocautery surgery and said upper panel member having a plurality of spaced apertures therethrough connecting with said closed area wherein the apertures through the upper panel member increase in number from a first end of said panel structure to a second opposite end thereof and there are more apertures located through said upper panel member at the second opposite end thereof than through the first end;
    connecting means projecting from said first end of said panel structure and in communication with the closed area in said panel structure;
    vacuum connector means for connecting said connecting means to vacuum drawing source means wherein a flow of air is created from above said upper panel member of said panel structure inwardly through the apertures in said upper panel member and the closed area.

2. The smoke aspirating device as claimed in claim 1, wherein said releasable securing means for said panel structure comprises a pressure sensitive adhesive coated over at least a portion of a lower surface of said lower panel member.

3. The smoke aspirating device as claimed in claim 1, wherein said upper and lower panel members are substantially flat and flexible.

4. The smoke aspirating device as claimed in claim 1, wherein said panel structure comprises support means to substantially maintain said upper and lower panel members vertically spaced with said closed area defined therebetween.

5. A smoke aspirating device for eliminating smoke generated during electrocautery surgery comprising:
    an elongated substantially flat and flexible panel structure having spaced elongated upper and lower panel members with a closed area defined therebetween, said lower panel member having releasable securing means for mounting said panel structure on the anatomy of a patient undergoing electrocautery surgery and said upper panel member having a plurality of spaced apertures therethrough connecting with said closed area;
    connecting means projecting from an end of said panel structure and in communication with the closed area in said panel structure;
    vacuum connector means for connecting said connecting means to vacuum drawing source means wherein a flow of air is created from above said upper panel member of said panel structure inwardly through the apertures in said upper panel member and the closed area; and
    wherein two substantially flat and flexible panel structures are adapted to be mounted on the anatomy of a patient undergoing electrocautery surgery on opposite sides of a surgery site, wherein said connecting means further including means for aligning and connecting said panel structures in parallel to said vacuum drawing source means.

6. The smoke aspirating device as claimed in claim 5, wherein said spaced apertures through said upper panel member extend over substantially the entire plan area of the upper panel member in an array to provide substantially uniform distribution of the flow of air and smoke over said panel structure.

7. A smoke aspirating device for eliminating smoke generated during electrocautery surgery comprising:
    an elongated substantially flat and flexible panel structure having vertically spaced elongated upper and lower panel members and lateral side walls extending between corresponding marginal edges of said panel members with a closed cavity defined therebetween, said lower panel member having pressure sensitive adhesive means over a lower surface thereof for securing said panel structure to a patient and said upper member having a plurality of spaced apertures therethrough connecting with said cavity arrayed to provide substantially uniform distribution of air and smoke flow over said panel structure, wherein said apertures through said upper panel member are increasing in number form a first end of said panel structure to a second opposite end thereof and more apertures are located through the second end of said upper panel member than through the first end thereof, said panel structure including support means for maintaining said upper and lower panel members vertically spaced with said cavity substantially therebetween;
    connecting means projecting from said first end of said panel structure and in communication with said cavity;
    suction means associated with said connecting means for drawing air and smoke inwardly through said apertures in said upper panel member and through said cavity in said panel structure.

8. The smoke aspirating device as claimed in claim 7, wherein two substantially flat and flexible panel structures are adapted to be mounted on the anatomy of a patient undergoing electrocautery surgery on opposite sides of a surgery site, said panel structures having said connecting means aligned for being connected in parallel to said suction means.

* * * * *